United States Patent
Campos et al.

(10) Patent No.: US 9,120,834 B2
(45) Date of Patent: Sep. 1, 2015

(54) MEMBRANE SEPARATION OF IONIC LIQUID SOLUTIONS

(71) Applicants: Daniel Campos, Atglen, PA (US); Andrew Edward Feiring, Wilmington, DE (US); Sudipto Majumdar, Newark, DE (US); Stuart Nemser, Wilmington, DE (US)

(72) Inventors: Daniel Campos, Atglen, PA (US); Andrew Edward Feiring, Wilmington, DE (US); Sudipto Majumdar, Newark, DE (US); Stuart Nemser, Wilmington, DE (US)

(73) Assignee: CMS TECHNOLOGIES HOLDINGS, INC., Newport, DE (US)

(*) Notice: Subject to any disclaimer, the term of this patent is extended or adjusted under 35 U.S.C. 154(b) by 0 days.

(21) Appl. No.: 14/527,732

(22) Filed: Oct. 29, 2014

(65) Prior Publication Data
US 2015/0119577 A1  Apr. 30, 2015

Related U.S. Application Data

(60) Provisional application No. 61/898,096, filed on Oct. 31, 2013.

(51) Int. Cl.
*C07F 9/54* (2006.01)
*B01D 61/36* (2006.01)
*B01D 71/80* (2006.01)
*B01D 71/36* (2006.01)
(Continued)

(52) U.S. Cl.
CPC ............ *C07F 9/5407* (2013.01); *B01D 61/362* (2013.01); *B01D 71/36* (2013.01); *B01D 71/80* (2013.01); *C07C 209/86* (2013.01); *C07C 213/10* (2013.01); *C07C 261/04* (2013.01); *C07C 303/44* (2013.01); *C07D 207/06* (2013.01); *C07D 213/18* (2013.01); *C07D 233/58* (2013.01)

(58) Field of Classification Search
None
See application file for complete search history.

(56) References Cited

U.S. PATENT DOCUMENTS

| 4,530,569 A | 7/1985 | Squire |
| 4,565,855 A | 1/1986 | Anderson et al. |

(Continued)

FOREIGN PATENT DOCUMENTS

| CN | 102956866 A | * | 3/2013 |
| WO | 00/12197 A1 | | 3/2000 |
| WO | 2012/064868 A2 | | 5/2012 |

OTHER PUBLICATIONS

Perry's Chemical Engineering Handbook, 8th ed., Doherty, M.F., et al., McGraw Hill Companies, Inc., 2008, pp. 13-9 to 13-13.

(Continued)

*Primary Examiner* — Chester Barry
(74) *Attorney, Agent, or Firm* — Jeffrey C. Lew

(57) ABSTRACT

A membrane separation process using a highly fluorinated polymer membrane that selectively permeates water of an aqueous ionic liquid solution to provide dry ionic liquid. Preferably the polymer is a polymer that includes polymerized perfluoro-2,2-dimethyl-1,3-dioxole (PDD). The process is also capable of removing small molecular compounds such as organic solvents that can be present in the solution. This membrane separation process is suitable for drying the aqueous ionic liquid byproduct from precipitating solutions of biomass dissolved in ionic liquid, and is thus instrumental to providing usable lignocellulosic products for energy consumption and other industrial uses in an environmentally benign manner.

16 Claims, 2 Drawing Sheets

(51) Int. Cl.
*C07D 233/58* (2006.01)
*C07D 213/18* (2006.01)
*C07C 209/86* (2006.01)
*C07D 207/06* (2006.01)
*C07C 213/10* (2006.01)
*C07C 261/04* (2006.01)
*C07C 303/44* (2006.01)

(56) References Cited

U.S. PATENT DOCUMENTS

| | | |
|---|---|---|
| 4,754,009 A | 6/1988 | Squire |
| 5,051,114 A | 9/1991 | Nemser et al. |
| 6,288,281 B1 | 9/2001 | Nemeth et al. |
| 6,361,582 B1 | 3/2002 | Pinnau et al. |
| 6,824,599 B2 | 11/2004 | Swatloski et al. |
| 8,182,557 B2 | 5/2012 | Argyropoulos |
| 8,293,112 B2 | 10/2012 | Nemser et al. |
| 8,506,815 B2 | 8/2013 | Nemser et al. |
| 2005/0205468 A1* | 9/2005 | Cadours et al. ............... 208/189 |
| 2009/0057224 A1 | 3/2009 | Huang et al. |
| 2011/0266220 A1 | 11/2011 | Campos et al. |
| 2011/0315541 A1* | 12/2011 | Xu ................. 203/18 |
| 2012/0116096 A1 | 5/2012 | Kalb |
| 2012/0157697 A1* | 6/2012 | Burket et al. ................. 549/489 |
| 2013/0292331 A1* | 11/2013 | Lipscomb et al. ............ 210/640 |
| 2014/0303408 A1* | 10/2014 | Zaher ............................ 568/913 |
| 2015/0122246 A1* | 5/2015 | Sun et al. |

OTHER PUBLICATIONS

Sun, Ning et al., Complete dissolution and partial delignification of wood in the ionic liquid 1-ethyl-3-methylimidazolium acetate The Royal Society of Chemistry, Green Chem., 11 (2009) 646-655.

Du, Xi Membrane Drying of Ionic Liquid (Ph.D. Thesis) Univ. of Toledo, Dec. 2012, 142 pages.

Garcia V., et al., Pervaporation recovery of [AMIM]Cl during wood dissolution; effect of [AMIM]Cl properties on the membrane performance J. Membr. Science 444 (2013) 9-15.

Sigma-Aldrich, Ionic Liquids, vol. 5, Article 6, http://www.sigmaaldrich.com/technical-documents/articels/chemfiles/ionic..., 2013, (downloaded Oct. 21, 2013), 5 pages.

Wang, Hui, et al. Ionic liquid processing of cellulose, Chem. Soc. Rev. 2012 (41) 1519-1537.

* cited by examiner

MEMBRANE SEPARATION OF IONIC LIQUID SOLUTIONS

Support was provided under Department of Energy grant DE-SC0011293, and Environmental Protection Agency grant EP-D-12-021. The U.S. government has rights in this patent application.

FIELD OF THE INVENTION

This invention relates to the membrane separation of water and small organic molecules (such as methanol, ethanol and acetone) from mixtures, including solutions, with ionic liquids using polymeric membranes comprising perfluorinated monomer repeat units, preferably perfluoro-2,2-dimethyl-1,3-dioxole, and optionally, additional fluorinated co-monomers.

BACKGROUND OF THE INVENTION

Ionic liquids (IL's) are considered as a relatively new and more environmentally benign generation of solvents for conducting chemical reactions or other processes than traditional volatile organic compounds (VOC's). ILs have high polarity, usually negligible vapor pressure and good solvent power for many organic and inorganic materials thereby facilitating chemical processes. Thus, they are potential replacements for VOCs in many industrial processes. However, many ILs are highly hygroscopic meaning that they readily absorb water from the atmosphere. It is well recognized that the presence of water in an IL can have a negative impact on its solvent properties. Furthermore, many procedures for isolating desirable products from ILs include adding large amounts of water which produces a solution of the IL in water. Because ILs are typically expensive materials, it is critical to provide an efficient and economical method for separating water from IL which will be effective with a wide range of water/IL compositions.

Kalb in US Patent Application Publication US2012/0116096 describes the utility of ionic liquids in many fields and the need for technology for removing water from IL. Kalb discloses adding an orthoester to react with the water contained in the ionic liquid and then removing the water/orthoester reaction products. However, this method results in the contamination of the IL with the orthoester and the reaction products.

Dissolution and processing of cellulose using ionic liquids is disclosed in U.S. Pat. No. 6,824,599 B2 (Swatloski, R. P. et al.). The reference relates to dissolving cellulose in an ionic liquid without derivatization, and regenerating it in a range of structural forms without requiring the use of harmful or volatile organic solvents. It also relates to controlling cellulose solubility and the solution properties by selecting the ionic liquid constituents, with small cations and halide or pseudohalide anions favoring solution.

Sun et al. (Green Chemistry, volume 11, pages 646-655, 2009) describe a process for upgrading biomass by dissolving wood in ionic liquids and then separately precipitating the cellulose and lignin components by the adding acetone/water and then removing the acetone. This process can contribute to the use of renewable resources. However, it leaves a solution of the ionic liquid in water. The authors point out that this process will require an industrially attractive method for removal of the water from the ionic liquid broth so that the ionic liquid can be fully recycled to reduce materials cost and so that the aqueous waste can be discharged in an environmentally acceptable manner.

Reverse osmosis (RO) and pervaporation are membrane separation methods that have been employed for drying of aqueous IL solutions. Du in "Membrane drying of ionic liquids" (PhD thesis, University of Toledo, December 2012) teaches dehydration using a commercial polyamide membrane by RO. Du's data presented in Table 1, below, shows that significant quantities of the IL (1-ethyl-3-methylimidazolium acetate) are lost in the permeate waste stream. Waste of expensive IL and the relatively high pressures required to achieve significant flux make this process uneconomical. Pervaporation mode membrane separations were also evaluated with commercial polysulfone membranes. Water flux decreased to zero at an IL content in the feed of 82%. A polyamide membrane was more successful at lower water concentration but showed a 150-fold decrease in water transport as the IL content of the feed increased from 81 to 97% (Table 2)

TABLE 1

| RO Pressure (psi) | Concentrated IL weight percent (%) | Concentrated IL flow rate (ml/min) | Permeate IL weight percent (%) | Permeate IL flow rate (ml/min) |
| --- | --- | --- | --- | --- |
| 350 | 5.44 | 8.5 | 0.30 | 1.5 |
| 400 | 5.57 | 8.4 | 0.33 | 1.6 |
| 450 | 6.47 | 8.2 | 0.33 | 1.9 |

TABLE 2

| IL Feed Concentration (wt. %) | Water flux (kg/hr/m$^2$) |
| --- | --- |
| 80.6 | 0.015 |
| 85.6 | 0.009 |
| 89.4 | 0.004 |
| 92.7 | 0.001 |
| 94.5 | 0.0003 |
| 97.5 | 0.0001 |

The literature reports the effects of exposing another common type of membrane to an ionic liquid on the membrane separation factor. For instance, Garcia, et al. reported in the Journal of Membrane Science 444 (2013) 9-15 the effects of exposing a polyvinyl alcohol (PVA) membrane to an ionic liquid at various temperatures and for different times on the water/butanol separation factor by pervaporation. Pertinent results of this paper are shown in Table 3, below. When the PVA membrane is exposed to ionic liquid at 40° C. from 1 to 5 days, the water/butanol separation factor is at least 196. However, when exposed to the ionic liquid at 60° C. for only one day, the separation factor drops to 13.9 and declines slightly with longer exposures. At 80° C. exposure the separation factor drops below 11 and continues to decline with longer exposures. This strongly suggests that the PVA membranes are unstable in the presence of ionic liquids.

TABLE 3

| Ionic liquid exposure temperature (° C.) | Ionic liquid exposure time (days) | Water/Butanol Separation Factor |
| --- | --- | --- |
| 40 | 1 | 196.9 |
| 40 | 3 | 207.2 |
| 40 | 5 | 241.3 |
| 60 | 1 | 13.9 |
| 60 | 3 | 9.4 |

TABLE 3-continued

| Ionic liquid exposure temperature (° C.) | Ionic liquid exposure time (days) | Water/Butanol Separation Factor |
|---|---|---|
| 60 | 3 | 9.8 |
| 60 | 3 | 10.1 |
| 60 | 5 | 10.4 |
| 80 | 1 | 10.9 |
| 80 | 3 | 5.8 |
| 80 | 5 | 3.6 |

It is known for example from Nemser et. al., U.S. Pat. No. 8,506,815, that pervaporation can remove water and methanol from conventional organic solvents using a fluoropolymer selectively permeable membrane. This patent does not disclose the separation of water from ILs. FIG. 1 is a semi-logarithmic plot of the activity coefficient (AC) of water in selected solvent/water mixtures as a function of respective solvent concentration in the mixture. Curves A-F are data for the water/tetrahydrofuran, water/acetic acid, water/isopropyl alcohol, water/ethyl alcohol, water/acetone, and water/methyl alcohol mixtures, respectively. Curve W is that of a typical water/IL (namely, water/1-ethyl-3-methylimidazolium acetate) mixture All of this plotted data except curve B was calculated using the Wilson model (Perry's Chemical Engineers' Handbook, 1999, pp 13-20, 13-21). for activity coefficient prediction. The ionic liquid/water solution data was determined from empirical measurements. FIG. 1 shows that mixtures of water and ILs have very different water activity coefficients than mixtures of water and common organic solvents. These data indicate that drying of ILs is much more difficult than drying of organic solvents.

Ethanol/water and tetrahydrofuran/water solution separation experiments by pervaporation were simulated at conditions of 80° C. with a Teflon® AF 1600 selectively permeable membrane copolymer of 65 mole % perfluoro-2,2-dimethyl-1,3-dioxole (PDD) and 35 mole % tetrafluoroethylene (TFE). Empirical permeation testing was performed to determine that this polymer achieves water permeance of 750 gas permeation units (GPU) and that the water/ethanol and the water/tetrahydrofuran selectivities are 15 and 50, respectively. A GPU is defined as 1 standard $cm^3/cm^2$-sec-cm Hg$\times 10^{-6}$. The simulations further assumed initial ethanol and tetrahydrofuran feed concentrations were 50 wt %. Results are summarized in Table 4 and show relatively moderate selectivities with significant loss of solvent. This level of solvent loss would be too high for the economical recovery of expensive ionic liquids.

Thus, there is a clear need for a membrane process for separating water from ionic liquids which shows high flux for water with minimal permeation of the costly ionic liquids, which operates effectively over a wide range of ionic liquid/water mixture concentrations and which is completely stable to the aggressive ionic liquid-containing fluid medium over a range of 50 to 100° C.

TABLE 4

| Solvent/Water System | Water/Solvent Selectivity | Final water wt % | Water/Solvent Separation Factor | Solvent Recovery % |
|---|---|---|---|---|
| Ethanol/Water | 15 | 20 | 6.1 | 77 |
| Ethanol/Water | 15 | 5 | 13.3 | 67 |
| Tetrahydrofuran/Water | 50 | 20 | 8.7 | 84 |
| Tetrahydrofuran/Water | 50 | 5 | 13.3 | 79 |

SUMMARY OF THE INVENTION

It has been discovered that certain selectively permeable perfluoropolymer membranes are highly effective in separating water from ionic liquids. These membranes have unexpectedly high water/IL separation factors, that are substantially higher than those observed for the same membrane compositions in water-organic solvent separations. These membranes are stable when exposed to ionic liquids and provide water flux that is at least 12 times greater than that of existing commercial membranes. The invention thus provides a membrane separation process for separating water from mixtures with ionic liquids to produce dehydrated ionic fluid suitable for industrial end uses. The invention also provides a membrane separation unit operation for removing ionic liquid from industrial process intermediate stream compositions that is essential for certain commercial uses such as the production of cellulose-based biomass for energy-producing end use applications.

This invention thus provides a method of separating water and an ionic liquid from a mixture thereof comprising the steps of (i) providing a separator with a membrane comprising a selectively permeable, nonporous layer comprising a highly fluorinated polymer, through which membrane water transfers preferentially relative to the ionic liquid, (ii) providing a feed of a liquid mixture comprising the ionic liquid and water in which the water is present at an initial concentration, (iii) permeating components of the feed through said membrane, thereby selectively removing water from the feed, and (iv) recovering from the separator a liquid retentate product comprising the water at a final concentration substantially lower than the initial concentration.

There is also provided an embodiment of the above-recited method adapted to enable the economic and environmentally benign harvesting of lignocellulose from natural woody biomass. It features the ability to separate lignocellulose from biomass with ionic liquids and subsequently to efficiently recover the ionic liquids used. This embodiment calls further for the steps of forming the feed of the liquid mixture by (a) providing biomass comprising lignocellulose, (b) mixing the biomass with the ionic liquid, (c) dissolving the lignocellulose in the ionic liquid thereby forming a solution, (d) adding an effective amount of water to the solution to selectively precipitate components of the biomass, thereby forming a heterogeneous mixture of precipitated solids and supernatant liquid (e) removing the supernatant liquid from the precipitated solids, and (f) using the supernatant liquid as the feed of the liquid mixture.

DETAILED DESCRIPTION OF THE INVENTION

Figure 1:
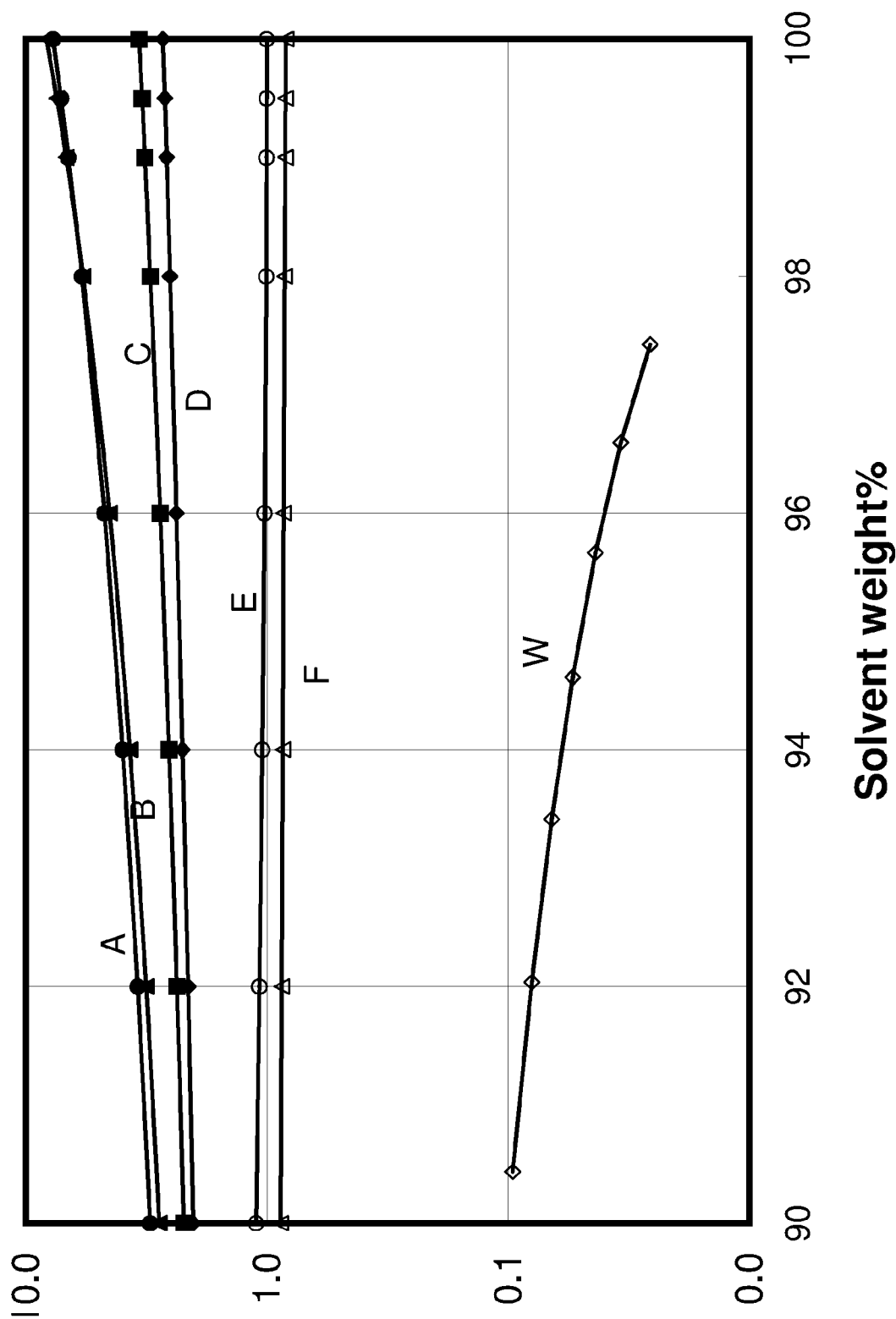
FIG. 1 is a semi-logarithmic plot of the water activity coefficient for various solvent/water mixtures vs. concentration of solvent component in each mixture.

The selectively permeable membranes effective for dehydrating ionic liquids according to this invention have an active layer that includes a highly fluorinated polymer. Preferably the highly fluorinated polymer includes repeating units of at least one polymerized perfluorinated monomer. Examples of such repeating units are the polymerized monomers perfluoro-2,2-dimethyl-1,3-dioxole (PDD), 2,2,4-trifluoro-5- trifluoromethoxy-1,3-dioxole (TTMD), perfluoro-2-methylene-4-methyl-1,3,dioxolane (PMD), perfluoro(4-vinyloxyl-1-butene) (PVOB), and perfluoro (alkenyl vinyl ether) (PFVE). PFVE polymer is commercially available from Asahi Glass, Japan, under the trademark Cytop®. Preference is given to highly fluorinated polymers that include polymerized PDD monomer.

The highly fluorinated polymer of the active layer composition can be a copolymer of fluorinated monomers. Preferably these fluorinated monomers include at least one of the perfluorinated compounds PDD, TTMD, PMD and PFVE. Other fluorinated monomers present in the copolymer may be perfluorinated or partially fluorine substituted. Examples of comonomers that can be copolymerized with the at least one perfluorinated monomer include perfluoromethyl vinyl ether (PFMVE) and acyclic olefins. Representative suitable acyclic fluorinated olefins are tetrafluoroethylene (TFE), chlorotrifluoroethylene (CTFE), vinyl fluoride (VF), vinylidene fluoride (VDF), and trifluoroethylene.

Usually the copolymer is a dipolymer or terpolymer of fluorinated comonomers. Preferred dipolymers include PDD/TFE copolymer (Teflon® AF, DuPont, Wilmington, Del.), and TTMD/TFE copolymer (Hyflon®, Solvay Solexis, Thorofare, N.J.), PDD/TFE copolymer is much preferred. Preferred terpolymers include those having any of PDD, TTMD, PMD and PFVE as the first comonomer, either TFE or CTFE as the second comonomer, and any of VF, VDF, PFMVE, PVOB and trifluoroethylene as the third comonomer. Preference is given to the PDD/TFE/(VF, VDF or trifluoroethylene) terpolymers.

Polymers utilizing perfluoro-2,2-dimethyl-1,3-dioxole monomer are particularly well suited for practice of the invention. Certain of the dioxole polymers and copolymers of PDD are reported in U.S. Pat. No. 5,051,114. These polymers are characterized by very high fractional free volume within the polymer, typically above 0.3. They are of low density compared with other crystalline fluoropolymers, i.e., below about 1.8 g/cm$^3$. They also are unusually very gas permeable, for instance, exhibiting pure gas permeabilities as high as 1,000 barriers or more for oxygen and as high as 2,000 barriers or more for hydrogen. One barrier equals $1 \times 10^{10}$ standard cm$^3$·cm/(cm$^2$·sec·cmHg).

In a preferred PDD/TFE, dipolymer embodiment the polymer typically contains 50-95 mole % of PDD, the complementary amount totaling 100 mole % being TFE. Examples of PDD-containing dipolymers are described in further detail in U.S. Pat. No. 4,754,009 of E. N. Squire, which issued on Jun. 28, 1988; and U.S. Pat. No. 4,530,569 of E. N. Squire, which issued on Jul. 23, 1985. Perfluorinated dioxole monomers are disclosed in U.S. Pat. No. 4,565,855 of B. C. Anderson, D. C. England and P. R. Resnick, which issued Jan. 21, 1986. The disclosures of all U.S. patent documents disclosed in this application are hereby incorporated herein by reference.

With respect to amorphous copolymers of PDD, the glass transition temperature will depend on the composition of the specific copolymer of the membrane, especially the amount of TFE or other comonomer that may be present. Examples of $T_g$ are shown in FIG. 1 of the aforementioned U.S. Pat. No. 4,754,009 of E. N. Squire as ranging from about 260° C. for dipolymers with 15% tetrafluoroethylene comonomer down to less than 100° C. for the dipolymers containing at least 60 mole % tetrafluoroethylene. It can be readily appreciated that perfluoro-2,2-dimethyl-1,3-dioxole copolymers according to this invention can be tailored to provide sufficiently high $T_g$ that a membrane of such composition can withstand exposure to a large range of temperatures, including as high as steam temperatures.

In preferred terpolymer embodiments, repeating units of perfluorinated monomers PDD, TTMD, PMD, and PFVE, typically are the predominant components of the active membrane layer composition and are thus present in total in the range of about 50-90 mole % of the copolymer. The total of TFE and CTFE comonomer repeating units is preferably about 5-40 mole % and repeating units of other comonomers usually are present in minor proportions, i.e., total of the other comonomers aggregating to about 5-10 mole %. Preferably the active layer, i.e., the selectively permeable portion, of the membrane should be non-porous. In preferred embodiments, the membrane is a composite structure comprising the active layer and a support layer that is coextensive and in direct contact with the active layer. The support layer can be laminated on or otherwise affixed to the active layer. Preferably, and especially for hollow fiber membranes the active layer can be coated on a surface of the microporous substrate. The substrate can be any microporous material that is chemically stable in presence of the feed composition. By "chemically stable" is meant that the substrate is able to maintain its structural integrity without significant degradation, decomposition or deterioration after enduring contact with components of the feed composition. By "microporous" is meant that the structure has pores throughout and that form continuous interstices or passageways extending from one side of the substrate through the thickness to the other side such that the feed can pass through the substrate indiscriminately. Many conventional, readily available and thus generally inexpensive, microporous membrane substrate materials can be used. Representative examples of porous substrate material are polymers selected from the group consisting of polyacrylonitrile (PAN), polyether ether ketone (PEEK), polyvinylidene fluoride (PVDF), polytetrafluoroethylene (PTFE), polypropylene, polysulfone (PSF) and polyether sulfone (PES).

Polysulfone and polyether sulfone have been surprisingly discovered to be very effective as microporous substrates in the novel composite membranes, i.e. membranes having an active layer of highly fluorinated polymer of this invention, such as PDD/TFE copolymer. It is recognized in the art that PSF and PES substrates of PDD/TFE copolymer membranes are not chemically resistant to good solvents, i.e., organic solvents such as ethanol, tetrahydrofuran, and methyl ethyl ketone, that are very effective at dissolving industrially important compounds. Ionic liquids are generally considered to be very good solvents. Thus it is unexpected to find that PDD/TFE copolymer and PSF or PES composite membranes exhibit remarkably good chemical resistance to ionic liquids such as 1-ethyl-3-methylimidazolium acetate (emim acetate), for example.

The invention is directed to the separation of water and small molecular compounds from mixtures with ionic liquids, ILs. Ionic liquids are a category of chemical compounds generally defined as salts having a melting point below 100° C. and typically below room temperature (i.e., <27° C.). Usually ionic liquids are salts of a predominantly organic cation and an inorganic anion. Other characteristics of ionic liquids include that they tend to be liquid over a wide temperature range, are not soluble in non-polar hydrocarbons, and are highly ionizing (but have a low dielectric strength). Ionic liquids have essentially no vapor pressure. Depending on the anion, they are miscible with water.

Some representative ionic liquids suitable for use in this invention include 1-allyl-3-methylimidazolium bis(trifluoromethanesulfonate), 1-ethyl-3-methylimidazolium acetate, 1-ethyl-3-methylimidazolium chloride, 1-ethyl-3-methylimidazolium bromide, 1-ethyl-3-methylimidazolium tetrafluoroborate, 1-ethyl-3-methylimidazolium hexafluorophosphate, 1-ethyl-3-methylimidazolium bis(trifluoromethanesulfonyl)imide, 1-ethyl-3-methylimidazolium ethylsulfate, 1-ethyl-3-methylimidazolium dicyanamide, 1-ethyl-3-methylimidazolium hydrogen sulfate, 1-ethyl-3-methylimidazolium diethyl phosphate, 1-butyl-3-methylimidazolium acetate, 1-butyl-3-methylimidazolium chloride, 1-butyl-3-methylimidazolium bromide, 1-butyl-3-methylimidazolium tetrafluoroborate, 1-butyl-3-methylimidazolium hexafluorophosphate, 1-butyl-3-methylimidazolium bis(trifluoromethanesulfonyl)imide, 1-butyl-3-methylimidazolium trifluromethansulfonate, 1-butyl-3-methylimidazolium ethylsulfate, 1,2-dimethoxyimidazolium hexafluorophosphate, 3-methyl-N-butylpyridinium chloride, trihexyl(tetradecyl)phosphonium methanesulfonate, trihexyl(tetradecyl)phosphonium chloride, tetrabutylphosphonium p-toluenesulfonate, tetrabutylphosphonium methanesulfonate, N,N,N-triethyl-N-(3,6-dioxaheptyl)ammonium acetate, tetrabutylammonium heptadecafluorooctanesulfonate, and N-butyl-N-methyl-pyrrolidinium bis(trifluoromethylsulfonyl)imide.

The term "small molecular compounds" means hydrophilic chemical compounds having a molecular weight of at most 100. The term "hydrophilic" in this context means that the compound is soluble in water at least about 5 wt %, (i.e., >5 parts by weight hydrophilic chemical compound/95 parts by weight water). A small molecular compound is further defined as having a vapor pressure greater than 50 mm Hg at 25° C. Representative examples of small molecular compounds suitable for separation according to this invention include acetone, methanol, ethanol, dichloromethane, ethyl acetate and mixtures thereof.

Figure 2:
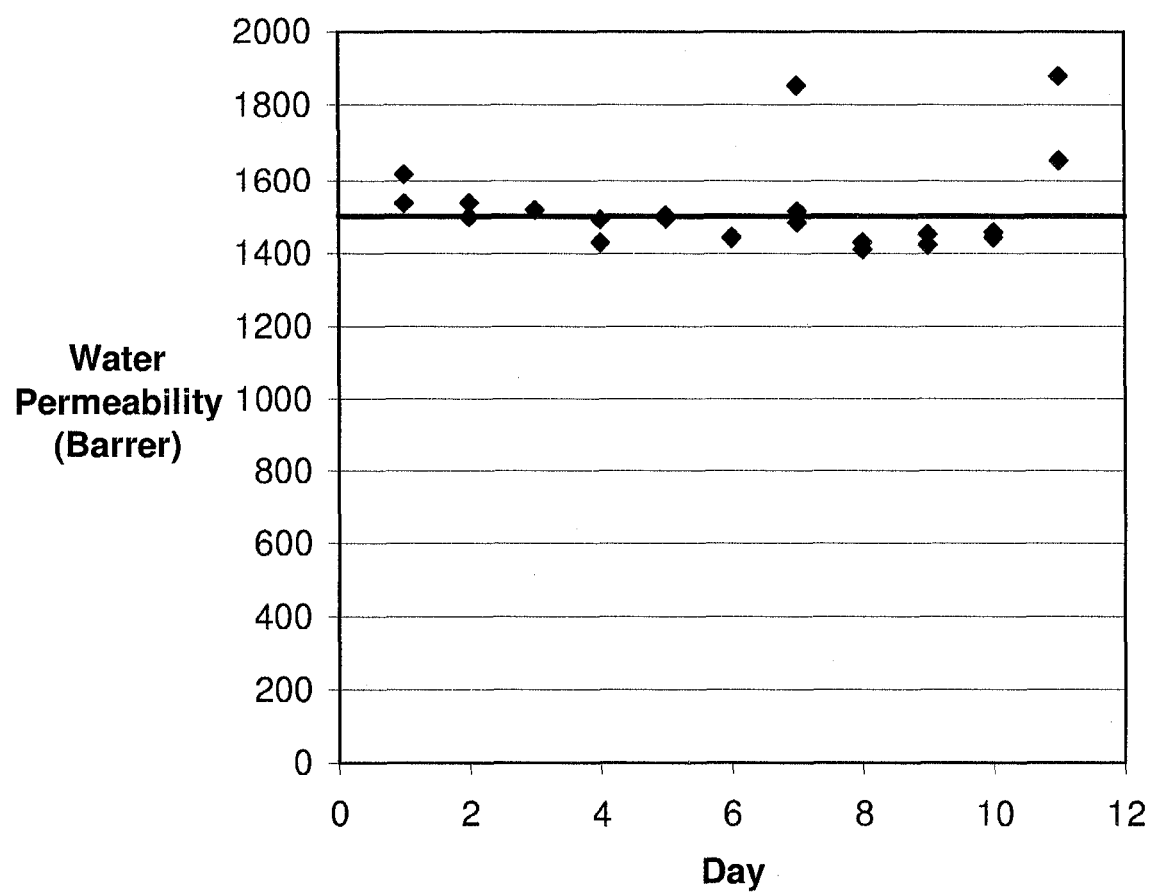
FIG. 2 is a plot of water permeability as a function of time during an extended dehydration of an aqueous ionic liquid solution according to an embodiment of this invention.

In one aspect, highly fluorinated polymer membranes able to rapidly remove water from ionic liquid with remarkable discrimination. That is, these polymer membranes demonstrate both high permeability and high selectivity. Table 5 presents data and FIG. 2 shows the results of an 11-day pervaporation experiment at 50 to 79° C. using a perfluorinated polymer membrane of Teflon AF 1600 for separating ionic liquid 1-ethyl-3-methylimidazolium acetate containing from 6 to 49% water. The membrane was a hollow fiber of porous polyether ether ketone (PEEK) on which a nonporous layer of the perfluorinated polymer was coated. Flow of feed to the membrane was 82-116 kg/h.

As seen in FIG. 2 the membrane maintained high water permeability despite exposure to ionic liquid at temperature up to 79° C. for 11 days. The extraordinary separation factors shown in Table 5 are very high. In many cases the separation factor was infinite because no IL was detected in the permeate. In view of the low water removal using PVA membranes in pervaporation on water-ionic liquid mixtures (Table 3) and the low water-solvent separation factors for Teflon AF 1600 (Table 4) these surprising results make possible the rapid dehydration of ionic liquids with extremely high separation factors and therefore high IL recoveries.

TABLE 5

| Day | Water Content (wt. %) | Temperature (° C.) | Water flux (kg/h/m$^2$) | Water permeability (Barrer) | Water/IL Separation Factor |
|---|---|---|---|---|---|
| 1 | 49 | 51 | 0.19 | 1578 | 2710 |
| 2 | 49 | 51 | 0.18 | 1517 | 3660 |
| 3 | 49 | 51 | 0.18 | 1516 | ∞ |
| 4 | 49 | 51 | 0.18 | 1490 | ∞ |
| 5 | 49 | 69 | 0.43 | 1493 | ∞ |
| 6 | 49 | 50 | 0.17 | 1440 | ∞ |
| 7 | 48 | 79 | 0.65 | 1482 | ∞ |
| 8 | 49 | 50 | 0.17 | 1410 | 5967 |
| 9 | 48 | 50 | 0.17 | 1450 | ∞ |
| 10 | 48 | 50 | 0.17 | 1449 | ∞ |
| 11 | 6 | 79 | 0.044 | 1767 | ∞ |

Use of PDD-containing fluorinated copolymers is also of great advantage in this invention because the selectivity of water relative to ionic liquids remains high, and substantially constant over a wide range of water concentration in the feed, usually in the range from about 5 wt % to about 95 wt % water. Membranes of these copolymers can also provide high selectivity relative to ionic fluids in the water concentration range of about 0.1 wt % to about 5 wt %. This is in contrast to many conventional membrane materials such as PVA that can exhibit very good selectivity for water relative to many organic compounds at water concentrations up to about 5 wt %, 10 wt % or 20 wt % depending on the substance being dehydrated. However, these conventional membranes typically suffer from significant selectivity decrease as the concentration of water increases and have very low selectivities in utilities where water is a major fraction of the solution being separated. By "major fraction" is meant that the component has the largest concentration of all components in a mixture. A major fraction is usually greater than 50% of the total mixture but can be less than 50% if all other components in the mixture each independently are of lower concentration than the major fraction component.

Due to the ability to maintain selectivity for preferential permeability of water from solutions, particularly those comprising ionic liquids over a wide, and nearly completed range of water compositions, highly fluorinated polymer membranes are extremely well suited for providing a single type unit operation for dehydration. That is, complete removal of water from an ionic liquid containing aqueous solution from a high concentration greater than about 50 wt %, 75 wt %, or 90 wt % water to less than about 10 wt %, 5 wt % or 1 wt % can be performed exclusively by membrane separation a system of highly fluorinated polymer membranes, preferably a PDD/TFE copolymer membrane.

The stability of perfluorinated polymer membranes to extended exposure to ionic liquids was also evaluated. Before and after the 11-day pervaporation experiment mentioned above, the membrane was subjected to selectivity measurements with various gases. Table 6 shows the results, which indicate that the membrane selectivity did not change significantly. Tables 6 shows that the Teflon AF membrane remains quite stable after exposure to ionic liquid at elevated temperatures.

TABLE 6

| | O2/N2 selectivity | He/N2 selectivity | CO2/N2 selectivity |
|---|---|---|---|
| Before | 2.6 | 12.4 | 6.3 |
| After | 2.7 | 12.2 | 6.4 |

Additional demonstration of the superior performance of perfluorinated polymer membranes in separation of water from ionic liquids was obtained by comparing performance of a PVA membrane and a PDD/TFE copolymer membrane. A PVA membrane was tested in the pervaporation of a solution of 1-allyl-3-methylimidazolium Cl ionic liquid containing 41% mole water at 60° C. as discussed in the Journal of Membrane Science 444 (2013) 9-15. For the purpose of comparison, the data from Table 3 was used to calculate the dehydration of an ionic liquid at the same conditions but with a Teflon AF membrane. The results are presented in Table 7 and show that the Teflon AF membrane has more than 12 times the water flux of the PVA membrane.

TABLE 7

| Membrane | Water flux (kg/h/m$^2$) |
| --- | --- |
| PVA | 0.0034 |
| Teflon AF | 0.044 |

In another significant aspect this invention provides a cost effective separation of water and selected organic solvents from ionic liquids that can be instrumental in the commercial development of processes for the conversion of lignocellulosic materials to useful fuels and chemicals. This commercially viable separation technique is thereby fundamental in facilitating the transition of raw materials for many industrial processes and consumer products from petroleum to renewable resources.

For example, it is known that certain ionic liquids can dissolve lignocellulose. In one process for recovering the lignocellulose contained in natural woody materials, the woody material is dissolved in an ionic liquid. Typically large proportions of water and organic, such as acetone, are added to the ionic liquid solution for purposes of isolating and obtaining high quality cellulosic products including cellulose and lignin. This inevitably forms a mixture of the ionic liquid and water that must be efficiently separated to recover the ionic liquid. If the ionic liquid is not dried, it becomes unusable and must be discarded as waste with considerable expense and potential risk of serious environmental damage. Thus without effective and economical water removal provided by separation utilizing highly fluorinated polymer membranes, this lignocellulose biomass recovery process would not be economically feasible. Thus, the membrane separation of this invention is deemed an integral part of the overall processes for environmentally benign conversion of biomass.

Selected substances were permeated through a PDD/TFE copolymer (Teflon AF) membrane to measure pure component permeabilities presented in Table 8. From that data the water/substance separation factors were calculated and are also shown in Table 8. While all of these gases and organic liquids have lower permeability than water, they have dramatically higher permeability than ionic liquids as seen by the separation factors through PDD/TFE copolymer calculated as permeability ratio of water/substance contrasted with the remarkably higher values of greater than than the 2710 for the ionic liquid/water reported in Table 5. This feature provides the enormous and serendipitous advantage that when processing water-ionic liquid systems containing other small organic liquid and/or gaseous components, a highly fluorinated polymer membrane, in particular a PDD/TFE copolymer membrane, can also remove the small organic liquid or gas while retaining the ionic liquid with excellent selectivity.

TABLE 8

| Substance | Permeability through PDD/TFE Copolymer (Barrers) | Separation Factor Water/Substance |
| --- | --- | --- |
| Water | 2000 | 1.0 |
| Acetonitrile | 800 | 2.5 |
| Methanol | 400 | 5.0 |
| Ethanol | 100 | 20 |
| Butanol | 40 | 50 |
| Isopropanol | 25 | 80 |
| Tetrahydrofuran | 22 | 91 |
| Helium | 1626 | 1.2 |
| Carbon dioxide | 919 | 2.2 |
| Oxygen | 366 | 5.5 |
| Nitrogen | 136 | 15 |

Although specific forms of the invention have been selected in the preceding disclosure for illustration in specific terms for the purpose of describing these forms of the invention fully and amply for one of average skill in the pertinent art, it should be understood that various substitutions and modifications which bring about substantially equivalent or superior results and/or performance are deemed to be within the scope of the following claims. All US patents and patent applications identified in this disclosure are hereby entirely incorporated by reference herein.

What is claimed is:

1. A method of separating an ionic liquid from a mixture comprising the steps of (i) providing the mixture that comprises ionic liquid and a liquid component selected from the group consisting of water, a small molecular compound and a blend thereof, (ii) providing a separator having a membrane comprising a selectively permeable, nonporous layer comprising a highly fluorinated polymer, through which membrane the liquid component transfers preferentially relative to the ionic liquid, (iii) providing a feed of the mixture in which the liquid component is present at an initial concentration, (iv) permeating components of the feed through the membrane, thereby selectively removing the liquid component from the feed, and (v) recovering from the membrane separator a liquid retentate product comprising the liquid component at a final concentration substantially lower than the initial concentration in which the highly fluorinated polymer comprises repeating units of a perfluorinated monomer selected from the group consisting of perfluoro-2,2-dimethyl-1,3-dioxole (PDD), 2,2,4-trifluoro-5-trifluoromethoxy-1,3-dioxole (TTMD), perfluoro-2-methylene-4-methyl-1,3,dioxolane (PMD), perfluoro(4-vinyloxyl-1-butene) (PVOB), perfluoro (alkenyl vinyl ether) (PFVE), and a mixture thereof.

2. The method of claim 1 in which the ionic liquid is a compound selected from the group consisting of 1-allyl-3-methylimidazolium bis(trifluoromethanesulfonate), 1-ethyl-3-methylimidazolium acetate, 1-ethyl-3-methylimidazolium chloride, 1-ethyl-3-methylimidazolium bromide, 1-ethyl-3-methylimidazolium tetrafluoroborate, 1-ethyl-3-methylimidazolium hexafluorophosphate, 1-ethyl-3-methylimidazolium bis(trifluoromethanesulfonyl)imide, 1-ethyl-3-methylimidazolium ethylsulfate, 1-ethyl-3-methylimidazolium dicyanamide, 1-ethyl-3-methylimidazolium hydrogen sulfate, 1-ethyl-3-methylimidazolium diethyl phosphate, 1-butyl-3-methylimidazolium acetate, 1-butyl-3-methylimidazolium chloride, 1-butyl-3-methylimidazolium bromide, 1-butyl-3-methylimidazolium tetrafluoroborate, 1-butyl-3-methylimidazolium hexafluorophosphate, 1-butyl-3-methylimidazolium bis(trifluoromethanesulfonyl)imide, 1-butyl-3-methylimidazolium trifluromethansulfonate, 1-butyl-3-methylimidazolium ethylsulfate, 1,2-dimethoxyimidazolium hexafluorophosphate, 3-methyl-N-butylpyridinium chloride, trihexyl(tetradecyl)phosphonium methanesulfonate, trihexyl (tetradecyl)phosphonium chloride, tetrabutylphosphonium p-toluenesulfonate, tetrabutylphosphonium methanesulfonate, N,N,N-triethyl-N-(3,6-dioxaheptyl)ammonium acetate, tetrabutylammonium heptadecafluorooctanesulfonate, N-butyl-N-methyl-pyrrolidinium bis(trifluoromethylsulfonyl)imide, and a mixture thereof.

3. The method of claim 1 in which the highly fluorinated polymer is a copolymer and further comprises repeating units of a fluorinated monomer selected from the group consisting of perfluoromethyl vinyl ether (PFMVE), a perfluorinated or partially fluorine substituted acyclic olefin and a mixture thereof.

4. The method of claim 3 in which the perfluorinated or partially fluorine substituted acyclic olefin is selected from the group consisting of tetrafluoroethylene (TFE), chlorotrifluoroethylene (CTFE), vinyl fluoride (VF), vinylidene fluoride (VDF), trifluoroethylene, and a mixture thereof.

5. The method of claim 1 in which the highly fluorinated polymer is a copolymer comprises (i) repeating units of a perfluorinated monomer selected from the group consisting of PDD, TTMD and PFVE, and (ii) repeating units of a fluorinated monomer selected from the group consisting of TFE, CTFE and a mixture thereof.

6. The method of claim 1 in which the highly fluorinated polymer comprises a terpolymer having a first comonomer selected from the group consisting of PDD, TTMD, and PFVE, a second comonomer selected from the group consisting of TFE and CTFE, and a third comonomer selected from the group consisting of PVOB, PMD, VF, VDF, PFMVE and trifluoroethylene.

7. A method of separating an ionic liquid from a mixture comprising the steps of (i) providing the mixture that comprises ionic liquid and a liquid component selected from the group consisting of water, a small molecular compound and a blend thereof, (ii) providing a separator having a membrane comprising a selectively permeable, nonporous layer comprising a highly fluorinated polymer, through which membrane the liquid component transfers preferentially relative to the ionic liquid, (iii) providing a feed of the mixture in which the liquid component is present at an initial concentration, (iv) permeating components of the feed through the membrane, thereby selectively removing the liquid component from the feed, and (v) recovering from the membrane separator a liquid retentate product comprising the liquid component at a final concentration substantially lower than the initial concentration in which the feed consists essentially of about 10-98 wt. % water and a complementary amount of ionic liquid and in which the method comprises recovering from said membrane separator a liquid retentate product of ionic liquid having a final concentration of less than about 5 wt % water.

8. A method of separating an ionic liquid from a mixture comprising the steps of (i) providing the mixture that comprises ionic liquid and a liquid component selected from the group consisting of water, a small molecular compound and a blend thereof, (ii) providing a separator having a membrane comprising a selectively permeable, nonporous layer comprising a highly fluorinated polymer, through which membrane the liquid component transfers preferentially relative to the ionic liquid, (iii) providing a feed of the mixture in which the liquid component is present at an initial concentration, (iv) permeating components of the feed through the membrane, thereby selectively removing the liquid component from the feed, and (v) recovering from the membrane separator a liquid retentate product comprising the liquid component at a final concentration substantially lower than the initial concentration in which the liquid component is water and is about 5-10 wt % of the feed, water is about 0.1-1 wt % of the retentate product, and in which the water permeance is greater than 800 GPU.

9. The method of claim 1 in which the mixture comprises at least 5 wt % of a small molecular compound having a permeance through the membrane in excess of about 10 GPU.

10. A method of separating an ionic liquid from a mixture comprising the steps of (i) providing the mixture that comprises ionic liquid and a liquid component selected from the group consisting of water, a small molecular compound and a blend thereof, (ii) providing a separator having a membrane comprising a selectively permeable, nonporous layer comprising a highly fluorinated polymer, through which membrane the liquid component transfers preferentially relative to the ionic liquid, (iii) providing a feed of the mixture in which the liquid component is present at an initial concentration, (iv) permeating components of the feed through the membrane, thereby selectively removing the liquid component from the feed, and (v) recovering from the membrane separator a liquid retentate product comprising the liquid component at a final concentration substantially lower than the initial concentration in which the selectively permeable, nonporous layer is coextensively in direct contact with a microporous substrate of a polymer consisting essentially of polysulfone (PSF), polyether sulfone (PES) and a mixture of them.

11. The method of claim 10 in which the highly fluorinated polymer is PDD/TFE copolymer.

12. A method of separating an ionic liquid from a mixture comprising the steps of (i) providing the mixture that comprises ionic liquid and a liquid component selected from the group consisting of water, a small molecular compound and a blend thereof, (ii) providing a separator having a membrane comprising a selectively permeable, nonporous layer comprising a highly fluorinated polymer, through which membrane the liquid component transfers preferentially relative to the ionic liquid, (iii) providing a feed of the mixture in which the liquid component is present at an initial concentration, (iv) permeating components of the feed through the membrane, thereby selectively removing the liquid component from the feed, and (v) recovering from the membrane separator a liquid retentate product comprising the liquid component at a final concentration substantially lower than the initial concentration in which the highly fluorinated polymer is PDD/TFE copolymer.

13. A method of separating an ionic liquid, from a mixture comprising the steps of (a) providing a biomass comprising lignocellulose, (b) mixing the biomass with the ionic liquid, (c) dissolving the lignocellulose in the ionic liquid thereby forming a solution, (d) adding an effective amount of water to the solution to selectively precipitate components of the biomass, thereby forming a heterogeneous mixture of precipitated solids and supernatant liquid having an initial concentration of water (e) removing the supernatant liquid from the precipitated solids, (f) providing a separator having a membrane comprising a selectively permeable, nonporous layer comprising a highly fluorinated polymer, through which membrane water transfers preferentially relative to the ionic liquid, (g) contacting a feed-retentate side of the membrane with the supernatant liquid (h) permeating components of the supernatant liquid through the membrane, thereby selectively removing water from the supernatant liquid, and (i) recovering from the feed-retentate side of the membrane a liquid retentate product comprising water at a final concentration substantially lower than the initial concentration, in which the highly fluorinated polymer comprises repeating units of a perfluorinated monomer selected from the group consisting of perfluoro-2,2-dimethyl-1,3-dioxole (PDD), 2,2,4-trifluoro-5-trifluoromethoxy-1,3-dioxole (TTMD), perfluoro-2-methylene-4-methyl-1,3,dioxolane (PMD), perfluoro(4-vinyloxyl-1-butene) (PVOB), perfluoro (alkenyl vinyl ether) (PFVE), and a mixture thereof.

14. The method of claim 13 in which the ionic liquid is a compound selected from the group consisting of 1-allyl-3-methylimidazolium bis(trifluoromethanesulfonate), 1-ethyl-3-methylimidazolium acetate, 1-ethyl-3-methylimidazolium chloride, 1-ethyl-3-methylimidazolium bromide, 1-ethyl-3-methylimidazolium tetrafluoroborate, 1-ethyl-3-methylimidazolium hexafluorophosphate, 1-ethyl-3-methylimidazolium bis(trifluoromethanesulfonyl)imide, 1-ethyl-3-methylimidazolium ethyl sulfate, 1-ethyl-3-methylimidazolium dicyanamide, 1-ethyl-3-methylimidazolium hydrogen sulfate, 1-ethyl-3-methylimidazolium diethyl phosphate, 1-butyl-3-methylimidazolium acetate, 1-butyl-3-methylimidazolium chloride, 1-butyl-3-methylimidazolium bromide, 1-butyl-3-methylimidazolium tetrafluoroborate, 1-butyl-3-methylimidazolium hexafluorophosphate, 1-butyl-3-methylimidazolium bis(trifluoromethanesulfonyl)imide, 1-butyl-3-methylimidazolium trifluromethansulfonate, 1-butyl-3-methylimidazolium ethylsulfate, 1,2-dimethoxyimidazolium hexafluorophosphate, 3-methyl-N-butylpyridinium chloride, trihexyl(tetradecyl)phosphonium methanesulfonate, trihexyl (tetradecyl)phosphonium chloride, tetrabutylphosphonium p-toluenesulfonate, tetrabutylphosphonium methanesulfonate, N,N,N-triethyl-N-(3,6-dioxaheptyl)ammonium acetate, tetrabutylammonium heptadecafluorooctanesulfonate, N-butyl-Nmethyl-pyrrolidinium bis(trifluoromethylsulfonyl)imide, and a mixture thereof.

15. The method of claim 13 in which the final concentration is less than about 5 wt % water.

16. The method of claim 13 in which further comprises adding to the solution a water soluble organic compound.

* * * * *